United States Patent
Samulski et al.

(10) Patent No.: US 6,204,059 B1
(45) Date of Patent: *Mar. 20, 2001

(54) AAV CAPSID VEHICLES FOR MOLECULAR TRANSFER

(75) Inventors: Richard Jude Samulski, Chapel Hill; Forrest K. Ferrari, Carrboro, both of NC (US)

(73) Assignee: University of Pittsburgh, Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/268,430

(22) Filed: Jun. 30, 1994

(51) Int. Cl.$^7$ ............................... C12N 7/01; C12N 15/00

(52) U.S. Cl. ..................... 435/456; 435/320.1; 435/440; 514/44

(58) Field of Search .............................. 435/320.1, 172.3, 435/456, 440; 935/32; 514/44

(56) References Cited

U.S. PATENT DOCUMENTS 4,797,368 * 1/1989 Carter et al. ...................... 435/320.1
5,354,678 * 10/1994 Lebkowski et al. .............. 435/172.3

OTHER PUBLICATIONS

Tratschin et al, Molec. Cell. Biol. 5: 3251 (1985).*
Flotte et al, J. Biol. Chem. 268: 3781 (1993).*
Rosenfeld et al, Cell 68: 143 (1992).*
Kirnbauer et al., 1993, "Efficient Self–Assembly of Human Papillomavirus Type 16L1 and L1–L2 into Virus–Like Particles," J. Virol. 67(12):6929–6936.
Hagensee et al., 1993, "Self–Assembly of Human Papillomavirus Type 1 Capsids by Expression of the L1 Protein Alone or by Coexpression of the L1 and L2 Capsid Proteins," J. Virol. 67(1):315–322.
Gonzalez, et al.,1993, "Assembly of the Matrix Protein of Simian Immunodeficiency Virus into Virus–like Particles," Virology 194:548–556.
Morgan et al., 1993, "Human Gene Therapy," Annu. Rev. Biochem. 62:191–217.
Ruffing et al., 1992,"Assembly of Virus like Particles by Recombinant Structural Proteins of Adeno–Associated Virus Type 2 in Insect Cells," J. Virol. 66:6922–6930.
Gossen et al., 1992, "Tight Control of Gene Expression in Mammalian Cells by Tetracycline–Responsive Promoters," Proc. Natl. Acad. Sci. 89:5547–5551.
Clemens et al., 1992, "Expression of Aleutian Mink Disease Parvovirus Capsid Proteins by a Recombinant Vaccinia Virus: Self–Assembly of Capsid Proteins into Particles," J. Virol. 66:3077–3085.

Berkner, K. L., 1992, "Expression of Heterologous Sequences in Adenoviral Vectors," Curr. Topics in Microbiology and Immunol. 158:39–66.
Muzyczka, N. 1992, "Use of Adeno–Associated Virus as a General Transduction Vector for Mammalian Cells," Curr. Topics in Microbiology and Immunol. 158:97–129.
Kajigaya et al., 1991, "Self–Assembled B19 Parvovirus Capsids, Produced in a Baculovirus System, are Antigenically and Immunologically Similar to Native Virons," Proc. Natl. Acad. Sci. USA 89:4646–4650.
Samulski et al., 1991, "Targeted Integration of Adeno–Associated Virus (AAV) into Human Chromosome 19," Emboj. 10:3941–3950.
Kotin et al., 1990, "Site–Specific Integration by Adeno–Associated Virus," Proc. Natl. Acad. Sci. USA 87:2211–2215.
Samulski et al., 1989, "Helper–Free Stocks of Recombinant Adeno–Associated Viruses: Normal Integration Does Not Require Viral Gene Expression," J. Virol. 63:3822–3828.
Dolph et al., 1988, "The Adenovirus Tripartite Leader May Eliminate the Requirement for Cap–Binding Protein Complex during Translation Initiation," J. Virol. 62(6):2059–2066.
Samulski et al., 1987, "A Recombinant Plasmid from Which an Infectious Adeno–Associated Virus Genome Can Be Excised In Vitro and Its Use To Study Viral Replication," J. Virol. 61(10):3096–3101.
Sanes et al., 1986, "Use of a Recombinant Retrovirus to Study Post–Implantation Cell Lineage in Mouse Embryos," EMBO 5:3122–3142.
Srivastava et al., 1983, "Nucleotide Sequence and Organization of the Adeno–Associated Virus 2 Genome," J. Virol.
Myers et al., 1980, "Assembly of Adeno–Associated Virus" Virology 102:71–82.
Hoggan et al., 1966, "Studies of Small DNA Viruses Found in Various Adenovirus Preparations: Physical, Biological, and Immunological Characteristics," Proc. Natl. Acad. Sci. 55:1467–1474.

* cited by examiner

Primary Examiner—James Martinell
(74) Attorney, Agent, or Firm—Pennie & Edmonds LLP

(57) ABSTRACT

The invention relates to the production of AAV capsids which may be used to transfer native or heterologous molecules into appropriate host cells. The capsid proteins can be expressed from a recombinant virus, expression vector, or from a cell line that has stably integrated the AAV capsid genes or coding sequences. The invention further provides for the production of AAV capsids in vitro from the AAV capsid proteins and the construction of packaged capsids in vitro. The invention further provides for the production of AAV capsids that have been genetically engineered to express heterologous epitopes of clinically important antigens to elicit an immune response.

3 Claims, 10 Drawing Sheets

AAV CAPSID VEHICLES FOR MOLECULAR TRANSFER

INTRODUCTION

The present invention relates to the production of adeno-associated virus (AAV) capsids in vivo or in vitro which may be used to transfer native or heterologous molecules into appropriate host cells. The invention further relates to the production of recombinant AAV capsids engineered to carry heterologous antigens for the stimulation of an immune response.

BACKGROUND OF THE INVENTION

The current interest in molecular replacement therapy as a modality for clinical treatment has necessitated the development of methods to safely and efficiently deliver genetic material or other molecules to cells. This has been attempted using physical means of cell permeation or by employing biological agents that naturally infect a host cell.

PHYSICAL TRANSFER METHODS

Methods to transfer DNA into a recipient cell include standard transfection techniques, mediated by calcium phosphate or DEAE-dextran, electroporation of accessible cells, and liposome-mediated transfer. These techniques are utilized in the research setting but require in vitro handling of the recipient cells and thus have limited clinical potential.

VIRAL VECTOR SYSTEMS

Viral vector systems exploit the efficiency of natural infection and use of DNA technology to engineer recombinant viruses that carry heterologous genes into the cell. Most clinical trials to date have taken this approach (Morgan, R. A. and W. F. Anderson, Annu. Rev. Biochem. 62:191–217, 1993).

Retroviral vectors have been most commonly used, chiefly because they can facilitate the integration of the carried DNA into the host cell genome, establishing stable integrants which are amplified during cellular DNA replication. However, this capability, while circumventing the limitations of transient gene expression, can result in the inadvertent activation of host genes or the interruption of cellular coding sequences due to random integration.

Adenoviral vectors can introduce DNA into a cell, but do not support the integration of the genetic material, which remains in episomal form in the nucleus and does not co-replicate with the cellular DNA. While adenoviruses are minor pathogens, their optimization as clinically relevant transfer vehicles may be limited to those tissues that are natural hosts for these viruses, i.e., the lungs (Berkner, K., Curr. Topics. Micro. Immunol. 158:39–66, 1992).

There is a clear need for safer delivery systems that combine the efficiency of viral infection with the potential to deliver genetic material to a targeted integration site in the host cell genome. There is also the need to be able to construct molecular delivery vehicles in vitro which can then be packaged in a cell-free system and which are capable of encapsidating a wide range of molecular constituents.

ADENO-ASSOCIATED VIRUS

AAV is a parvovirus that can assume two pathways upon infection of a host cell. In the presence of helper virus, AAV will enter the lytic pathway where the viral genome is transcribed, replicated, and encapsidated into newly formed viral particles. In the absence of helper virus function, the AAV genome becomes integrated as a provirus into a specific region of the host cell genome, through recombination between the AAV termini and host cell sequences. Characterization of the proviral integration site and analysis of flanking cellular sequences indicates specific targeting of AAV viral DNA into the long arm of human chromosome 19 (Kotin, R. M., et al., Proc. Natl. Acad. Sci. USA 87:2211–2215, 1990; Samulski, R. J., et al., EMBO J. 10:3941–3950, 1991). This particular feature of AAV reduces the likelihood of insertional mutagenesis resulting from random integration of viral vector DNA into the coding region of a host gene. Furthermore, in contrast to the retroviral LTR sequences, the AAV ITR sequences appear to be devoid of transcriptional regulatory elements, reducing the risk of insertional activation of protooncogenes.

The AAV genome is composed of a linear single stranded DNA molecule of 4680 nucleotides which contains major open reading frames coding for the Rep (replication) and Cap (capsid) proteins. Flanking the AAV coding regions are two 145 nucleotide inverted termini (ITR) repeat sequences that contain palindromic sequences that can fold over to form hairpin structures that function as primers during initiation of DNA replication. In addition to their role in DNA replication, the ITR sequences have been demonstrated to be necessary for viral integration, rescue from the host genome and encapsidation of viral nucleic acid into mature virions (Muzyczka, N., Curr. Top. Micro. Immunol. 158:97–129, 1992).

The capsids have icosahedral symmetry and are about 20–24 nm in diameter. They are composed of three proteins (VP1, VP2, and VP3, which are approximately 87, 73 and 61 Kd, respectively) (Muzyczka, N., Curr. Top. Micro. Immunol. 158:97–129, 1992). VP3 represents 90% of the total virion protein; VP2 and VP1 account for approximately 5% each. All capsid proteins are N-acetylated.

RECOMBINANT PRODUCTION OF VIRAL CAPSIDS

Recombinant DNA technology has been used to isolate the genes for structural proteins of many viruses. For example, vaccinia virus has been used to carry the structural genes for human papilloma virus 1 (Hagensee, M. E., et al., J. Virol. 67:315–322, 1993); simian immunodeficiency virus (Gonzalez, S. A., et al., Virology 194:548–556, 1993); and Aleutian mink disease parvovirus (Clemens, D. L., et al., J. Virol. 66:3077–3085, 1992); capsid formation has been detected in all systems. Baculovirus vectors have been used for the expression of the structural proteins of human papilloma virus (Kirnbauer, R., et al., J. Virol. 67:6929–6936, 1993) and B19 parvovirus (Kajigaya, S., et al., Proc. Natl. Acad. Sci. 88:4646–4650, 1991); these proteins have assembled into capsids within the infected cells. Baculovirus-mediated expression of the capsid proteins of adeno-associated virus-2 (Ruffing, M., et al., J. Virol. 66:6922–6930, 1992) resulted in the formation of capsids with an altered stoichiometry from wild-type capsids and which failed to localize into the nuclear clusters observed in a wild-type infection.

These efforts have been expended to study virus life-cycles and do not use of any of these systems to encapsidate foreign genomes or other materials for delivery in vivo.

SUMMARY OF THE INVENTION

The invention relates to the production of AAV capsids which may be used to transfer native or heterologous molecules into appropriate host cells. The capsid proteins can be expressed from a recombinant virus, expression vector, or from a cell line that has stably integrated the AAV capsid genes or coding sequences. The invention further provides for the production of AAV capsids in vitro from the AAV capsid proteins and the construction of packaged capsids in vitro. The invention further provides for the production of AAV capsids that have been genetically engineered to express heterologous epitopes of clinically important antigens to elicit an immune response.

Molecules which may be associated with or encapsidated into capsids include DNA, RNA, proteins, peptides, small organic molecules, or combinations of the same. The AAV capsids can accommodate nucleic acids which are quite large e.g., 5000 bp, and therefore, may be advantageously used for the transfer and delivery of large genes and genomic sequences. Because the AAV inverted terminal repeats (ITRs) are responsible for the ability of the AAV genome to integrate into the host cell genome (Samulski, R. J., et al., EMBO J. 10:3941–3950, 1991), these sequences may be used with the heterologous DNA in order to provide for integration of the heterologous DNA into the host cell genome and may further facilitate packaging into an AAV capsid.

The invention is demonstrated by way of examples in which the AAV capsid is produced from a recombinant adenovirus engineered to carry the capsid genes. This system may be particularly advantageous in AAV gene delivery systems because adenovirus serves as a natural helper for AAV infection. Upon infection of the host cell, expression of the capsid proteins is followed by assembly of the AAV capsid.

DETAILED DESCRIPTION OF THE INVENTION

Figure 1:
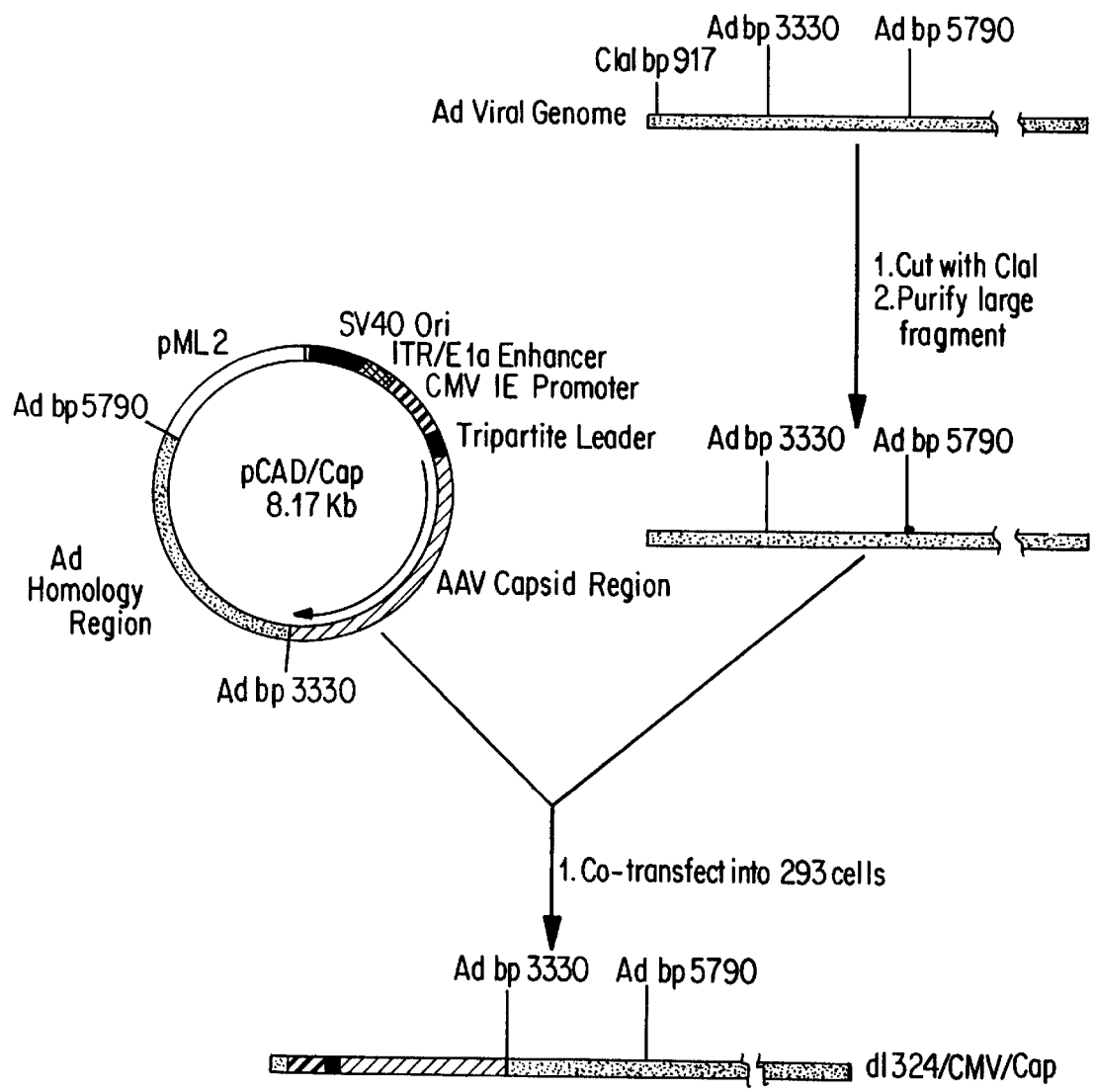
FIG. 1. Representation of d1324/CMV/Cap construction.

The invention relates to methods for producing AAV capsids which may be used to transfer molecules for molecular replacement therapy. Methods for the intracellular production of AAV capsids provided include vector-mediated expression systems and cell-line expression systems for the generation of capsids. Methods for the in vitro construction of AAV capsids and for the in vitro packaging of these capsids are also provided. The invention is also directed to the production of AAV capsids which are engineered to carry heterologous epitopes that can elicit an immune response in vivo.

AAV CAPSID PROTEINS

The AAV capsids of the present invention are produced by the expression of the three capsid genes, VP1, VP2, and VP3, and the subsequent assembly of these proteins into the AAV capsid particle.

The AAV capsid genes are found in the right-hand end of the AAV genome, and are encoded by overlapping sequences of the same open reading frame through the use of alternative initiation codons. A 2.6 kb precursor mRNA is alternatively spliced into two 2.3 kb transcripts. Both VP2 and VP3 can be produced from either transcript with the use of different translation initiation signals, while VP1 can only be translated from one of the transcripts. The fact that overlapping reading frames code for the three AAV capsid proteins results in the obligatory expression of all capsid proteins in a wild-type infection.

In accordance with the invention the open reading frame which encodes the entire AAV VP1, VP2 and VP3 capsid proteins may be engineered into expression vectors. The use of a gene sequence that encodes the three overlapping reading frames may result in a level and pattern of expression of the capsid proteins that mimics the wild-type infection and generates wild-type AAV capsids. The disadvantage of this approach is that the capsid composition cannot be regulated or altered.

Alternatively, multiple vectors may be used to separately introduce each of the capsid genes into expression host cell. The use of AAV capsid CDNA gene sequences allows for construction of separate expression vectors which may be introduced into the cell alone or together, and may also be quantitatively controlled. Such control may be achieved by the amount of a vector introduced into a cell, or, alternatively, individual vectors may employ specific promoters that are chosen for strength of expression of a linked capsid gene. Thus, the stoichiometry and composition of the AAV capsids may be regulated. A disadvantage of this approach is that the natural stoichiometry of the capsid proteins in a wild-type infection may not be achieved for optimal assembly into capsids.

The sequences of the capsid genes are reported in Srivastava, A., et al., 1983, J. Virol. 45:555–564; Muzyczka, N., 1992, Curr. Top. Micro Immunol. 158:97–129, and Ruffing, M., et al., 1992, J. Virol. 66:6922–6930, 1992. Sources for the AAV capsid genes may include the mammalian virus serotypes AAV-1, AAV-2, AAV-3, AAV-4, and AAV-5, as well as bovine AAV and avian AAV. The invention contemplates, in addition to the capsid DNA sequences disclosed therein, (1) any DNA sequence that encodes the same amino acid sequence for capsid VP1, VP2 and VP3 shown in Srivastava, A., et al., supra; Muzyczka, N., supra and Ruffing, M., et al. supra; (2) any DNA sequence that hybridizes to the complement of the coding sequences disclosed therein under highly stringent conditions, e.g., washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or 3) any DNA sequence that hybridizes to the complement of the coding sequences disclosed therein under less stringent conditions, such as moderately stringent conditions, e.g., washing in 0.2×SSC/0.1% SDS at 42° C. (Ausubel et al., 1989, supra), yet which still encodes a functionally equivalent gene product.

The invention also encompasses 1) DNA vectors that contain any of the coding sequences disclosed herein and/or their complements (i.e., antisense); 2) DNA expression vectors that contain any of the coding sequences disclosed herein and/or their complements (i.e., antisense), operatively associated with a regulatory element that directs the expression of the coding and/or antisense sequences; and (3) genetically engineered host cells that contain any of the coding sequences disclosed herein and/or their complements (i.e., antisense), operatively associated with a regulatory element that directs the expression of the coding and/or antisense sequences in the host cell. Regulatory elements include but are not limited to inducible and non-inducible promoters, enhancers, operators and other elements known to those skilled in the art that drive and regulate expression. The invention includes fragments of any of the DNA sequences disclosed herein.

Alternatives to isolating a capsid gene sequence include, but are not limited to, chemically synthesizing the gene sequence from a known sequence or making cDNA to the RNA which encodes the capsid proteins. Other methods are possible and within the scope of the invention.

Nucleic acids which encode derivatives (including fragments) and analogs of native capsid proteins can also be used in the present invention, as long as such derivatives and analogs retain the ability to assemble into an AAV capsid. In particular, capsid derivatives can be made by altering capsid sequences by substitutions, additions, or deletions that provide for functionally active molecules. Furthermore, due to the degeneracy of nucleotide coding sequences, other DNA sequences which encode substantially the same or a functionally equivalent AAV capsid amino acid sequence may be used in the practice of the methods of the invention. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the ampipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine.

IN VIVO PACKAGING SYSTEMS

AAV capsid genes may be expressed from the recombinant expression vectors or from an engineered cell line so that the proteins are able to assemble into the capsid within the cell.

Recombinant Expression of AAV Capsid Proteins and Capsid Formation

The invention can be facilitated with the use of a number of viruses or vectors which can be engineered to carry the genes for the AAV capsid proteins. Recombinant viruses or vectors will be used to infect or transfect appropriate host cells, and the expression of the AAV proteins will commence, resulting in the production of adequate levels of the capsid proteins to facilitate capsid formation.

In a preferred embodiment, the virus for the construction of a recombinant virus is a virus which is a natural helper for wild-type AAV infection. Such viruses could include herpesviruses or adenoviruses. Since these viruses are required for gene expression by a wild-type AAV, their use as the recombinant carrier for the AAV capsid proteins may be optimal for the production of appropriate levels and ratios of the three capsid proteins since they may be facilitating these processes in the wild-type infection.

In a specific embodiment, adenovirus is used as the recombinant virus. Deletion strains of adenovirus can accommodate the insertion of the heterologous material, i.e., the AAV capsid coding region, into non-essential regions of the adenovirus such as E1 or E3. Infection of adenovirus into a complementing host cell line, such as the 293 line, will allow the expression of the AAV capsid proteins and the subsequent assembly of these into the capsid vehicle. Heterologous promoters for the capsid genes may be used, including but not limited to CMV, pGK, beta actin, RSV, SV40, and transthyretin liver specific promoter. Host cells may include AS49, HeLa, Cos-1, KB and Vero.

Recombinant vaccinia virus can be produced by homologous recombination between a plasmid carrying the capsid genes and wild-type vaccinia virus within a host cell. Expression of these genes by the recombinant virus results in the assembly of the proteins into the capsids. Host cells may include CV1, HeLa, BSC-40, BSC-1 and TK-$^-_{143B}$.

In another embodiment of the invention, baculovirus vectors may be constructed to carry the AAV capsid coding region by engineering these genes into the polyhedrin coding region of a baculovirus vector and producing viral recombinants by transfection into a baculovirus-infected cell. These viruses can express the AAV capsid proteins and facilitate the production of the capsids subsequently. Host cells may include Sf9 and Sf24.

In another embodiment of the invention, recombinant expression vectors may be used which are engineered to carry one or more of the AAV capsid genes into a host cell to provide for expression of the AAV capsid proteins.

Such vectors may be introduced into a host cell by transfection with calcium-phosphate or DEAE-dextran, or by electroporation or liposome-mediated transfer.

Recombinant expression vectors include, but are not limited to, COS cell-based expression vectors such as CDM8 or pDC201, or CHO cell-based expression vectors such as pED vectors.

The capsid coding region may be linked to any number of promoters in an expression vector that can be activated in the chosen cell line. Additionally, this cassette (capsid genes and promoter) is carried by a vector that contains a selectable marker so that cells receiving the vector may be identified.

Promoters to express the capsid proteins within a cell line may be drawn from those that are functionally active within the host cell. They may include, but are not limited to, the CMV promoter, the SV40 early promoter, the herpes TK promoter, and others well known in recombinant DNA technology. Inducible promoters may be used, including but not limited to, the metallothionine promoter (MT), the mouse mammary tumor virus promoter (MMTV), and others known to those skilled in the art.

Selectable markers and their attendant selection agents can be drawn from the group including but not limited to aminoglycoside phosphotransferase/G418, hygromycin-B phosphotransferase/hygromycin-B, and amplifiable selection markers such as dihydrofolate reductase/methotrexate and others known to skilled practitioners.

Other embodiments of the present invention include the use of procaryotic, insect, plant, and yeast expression systems to express the AAV capsid proteins. In order to express capsid proteins the nucleotide sequence coding for the capsid proteins, or a functional equivalent as described in Section 5.1, supra, are inserted into an appropriate expression vector, i.e., a vector which contains the necessary elements for the transcription and translation of the inserted coding sequences. Methods which are well known to those skilled in the art can be used to construct expression vectors containing the capsid protein coding sequences operatively associated with appropriate transcriptional/translational control signals. These methods include in vitro recombinant DNA techniques, synthetic techniques, and in vivo recombination/genetic recombination. See, for example, the techniques and vectors described in Maniatis, et al., 1989, Molecular Cloning, A Laboratory Manual, Cold Spring Harbor Laboratory, N.Y. and Ausubel et al., 1989, Current Protocolsin Molecular Biology, Greene Publishing Associates & Wiley Interscience, N.Y.

A variety of prokaryotic, insect, plant and yeast expression vector systems (i.e.-vectors which contain the necessary elements for directing the replication, transcription, and translation of capsid coding sequences) may be utilized equally well by those skilled in the art, to express capsid coding sequences. These include but are not limited to microorganisms such as bacteria transformed with recombinant bacteriophage DNA, plasmid DNA or cosmid DNA expression vectors containing the capsid coding sequences; yeast transformed with recombinant yeast expression vectors containing the capsid coding sequences; insect cell systems infected with recombinant virus expression vectors (e.g., baculovirus) containing the capsid coding sequences; plant cell systems infected with recombinant virus expression vectors (e.g., cauliflower mosaic virus CaMV; tobacco mosaic virus, TMV) or transformed with recombinant plasmid expression vectors (e.g., Ti plasmid) containing the capsid coding sequences.

The expression elements of these vectors may vary in their strength and specificities. Depending on the host/vector system utilized, any one of a number of suitable transcription and translation elements may be used.

Specific initiation signals are also required for sufficient translation of inserted protein coding sequences. These signals include the ATG initiation codon and adjacent sequences. These exogenous translational control signals and initiation sequences can be of a variety of origins, both natural and synthetic. For example, E. coli expression vectors will contain translational control sequences, such as an appropriately positioned ribosome binding site and initiation ATG. The efficiency of expression may be enhanced by the inclusion of transcription attenuation sequences, enhancer elements, etc.

An alternative expression system which could be used to express AAV capsid proteins is an insect system. In one such system, Autographa californica nuclear polyhidrosis virus (AcNPV) is used as a vector to express foreign genes. The virus grows in Spodoptera frugiperda cells. The AAV capsid coding sequences may be cloned into non-essential regions (for example the polyhedrin gene) of the virus and placed under control of an AcNPV promoter (for example the polyhedrin promoter). Successful insertion of the AAV capsid coding sequences will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed.

In any of these embodiments, the capsid proteins may assemble into an AAV capsid intracellularly, or, alternatively, the proteins may be isolated from the expression system for construction of the AAV capsids in vitro.

Detection of the AAV capsid proteins produced in the above embodiments of the invention can be performed by standard techniques including Northern analysis to detect expression of mRNA, and protein-based detection techniques such as immunoblotting or immunoprecipitation. Detection of the AAV capsids can be accomplished by subjecting a lysate from infected cells to isopycnic centrifugation to concentrate the viral particles at the proper gradient density. Further confirmation of the presence of the viral capsids can be ascertained by transmission electron microscopy to visualize and measure the particles.

Cell Lines Engineered To Produce AAV Capsids

A cell line may be engineered that will natively express the three AAV capsid proteins, which will then assemble into an AAV capsid.

To engineer an AAV-capsid producing cell line, cells are tranfected with a vector into which the AAV capsid open reading frame has been inserted. Alternatively, each capsid protein coding region may be engineered into separate vectors and used to transfect host cells. Transfection may be accomplished with any of the standard techniques in the art. Alternatively, a cell line can be established with the use of viral vectors that are capable of integrating DNA into the host cell genome. Examples of these vectors include those derived from retroviruses or AAV.

Cell lines which may be chosen for integration include but are not limited to HeLa, COS, NIH 3T3, and others well known to those skilled in the art. The capsid coding region may be linked to any number of heterologous promoters that can be activated in the chosen cell line. Additionally, this insertion cassette (capsid genes and promoter) may be linked to a gene coding for a selectable marker, in which case the integration of the capsid coding region with the linked marker will confer the particular phenotype afforded by the marker to a stably transfected cell. Thus, the cells that have successfully integrated the capsid genes will be selectable. Alternatively, the selectable marker may be transfected on a separate plasmid.

Promoters to express the capsid proteins within a cell line may be drawn from those that are functionally active within the host cell. They may include, but are not limited to, the CMV promoter, the SV40 early promoter, the herpes TK promoter, and others well known in recombinant DNA technology. Inducible promoters may be used, including but not limited to, the metallothionine promoter (MT), the mouse mammary tumor virus promoter (MMTV), and others known to those skilled in the art.

Selectable markers and their attendant selection agents can be drawn from the group including but not limited to aminoglycoside phosphotransferase/G418, hygromycin-B phosphotransferase/hygromycin-B, and amplifiable selection markers such as dihydrofolate reductase/methotrexate and others known to skilled practitioners.

Stable expressing cell lines may also be constructed by linking the AAV ITR sequence to an expression cassette containing the capsid coding region with the appropriate transcriptional signals to allow for integration into the host cell genome.

Standard recombinant DNA techniques may be used to construct the recombinant viruses and vectors (Ausubel, F. et al., eds., Current Protocols in Molecular Biology, Wiley & Sons, New York, 1994).

Detection of the expression of the capsid genes can be performed by standard techniques including Northern analysis, immunoblotting, and immunoprecipitation. Detection of the production of the viral capsids can be accomplished by subjecting a cell lysate to isopycnic centrifugation wherein the viral particles will band according to their density. Further confirmation of the presence of the viral capsids can be ascertained by transmission electron microscopy to measure and visualize the particles.

Sources for the AAV capsid genes may include the mammalian virus serotypes AAV-1, AAV-2, AAV-3, AAV-4, and AAV-5, as well as bovine AAV and avian AAV.

MANIPULATIONS OF AAV CAPSID VEHICLES

AAV capsids are constructed in vitro from the AAV capsid proteins and these vehicles can be used to deliver molecular constituents into a target cell. In another embodiment, the AAV capsids are recovered from a cell and packaged in vitro with the desired constituents. In a yet another embodiment, AAV capsid produced intracellularly can be packaged in vivo with DNA introduced into the same cell or other intracellular molecular constituents.

Intracellular Formation of Packaged Capsids

In this embodiment of the present invention, the AAV capsids produced intracellularly by any of the methods described in Section 5.2., supra, may be packaged within the cell with any number of molecular constituents. DNA introduced into the cell which expresses the capsid proteins may be packaged into an AAV capsid, and this DNA may be advantageously linked to the AAV ITR to increase the efficiency of packaging. Other molecular constituents, such as RNA, proteins, peptides, or small organic molecules that are either introduced into the cell or are naturally found intracellularly may also be packaged into the AAV capsid within the cell.

In Vitro Packaging of AAV Capsids

In this embodiment, AAV capsids are isolated by standard methods for the recovery of AAV virions. Cells engineered to express the AAV capsid proteins as described in Sections 5.1 and 5.2 supra, or cells infected with recombinant viruses carrying the AAV capsid genes or cells infected with wild-type AAV in a helper-virus background are collected by centrifugation and subjected to freeze-thaw cycles that separate viral material from the cells. The lysate is subjected to isopycnic centrifugation (CsCl) and the particles are recovered from the appropriate band on the gradient. This sample is subjected to a second round of CsCl centrifugation, and fractions from the gradient are recovered and analyzed for the presence of the AAV capsid proteins by Western Blot analysis. The gradient density of these enriched fractions will determine the nature of the viral particles that are banded. Fractions which show the presence of the three capsid proteins are those that are enriched with the viral capsids. Further confirmation of capsid production can be obtained by subjecting an aliquot of the enriched fractions to transmission electron microscopy to visualize the AAV capsids.

The capsids may be disassembled by known techniques for the dissociation of macromolecular protein structures, including denaturation with urea or guanidium hydrochloride, heat, or pH manipulation. Where structural integrity is dependent on disulfide bond formation, mercaptoethanol or any thiol reducing agent will cause covalent disulfide bond rupture.

Reassembly of the AAV capsid with the desired constituents is accomplished by co-incubation of the capsid proteins with the materials to be packaged. Favorable conditions for reassembly include manipulations of pH, temperature, and buffer conditions that are well known to one skilled in the art.

In the specific embodiment in which DNA is to be packaged, the molecule may be linked to the AAV ITR signal for optimal encapsidation and for integration of the DNA into the host cell genome.

In Vitro Assembly of AAV Capsids

In this embodiment of the invention, the three AAV capsid proteins may be isolated in vitro and combined to form the AAV capsid. The proteins may be recovered from lysates of virus-infected cells or from pure preparations of AAV virus. Alternatively, the proteins may be recovered from cells infected with recombinant virus carrying the AAV capsid genes, or from cells engineered to stably express the capsid proteins.

Recovery of the capsid proteins from any of the above sources may be accomplished by the use of known techniques for protein isolation, i.e., affinity chromatography, ion-exchange chromatography, gel-filtration chromatography, or HPLC (Creighton, T. E., Proteins, W. H. Freeman and Company, New York, 1984).

With the AAV capsid proteins so isolated, they may be combined in vitro so as to mimic the levels of the proteins found in the AAV virion and therefore facilitate the reconstitution of the capsid. In this embodiment of the invention, VP3 is the major constituent of the in vitro reaction since it accounts for about 90% of the virion protein, and VP2 and VP1 are each present is lesser amounts, about 5% each, corresponding to their quantitative presence as a component of the virion. Alternatively, the proteins may be combined in an equimolar ratio for the formation of the capsid. Optimization for the formation of the capsids may rely on the parameters of pH, temperature, or buffer conditions, and are known to those skilled in the art.

The capsid proteins may be also combined with the constituents to be packaged into the viral particle to allow for assembly and packaging simultaneously. In this embodiment, the constituent may be native or heterologous DNA to which the AAV packaging signal is attached. Alternatively, the constituents may include DNA, RNA, proteins, or peptides which can be associated with, or encapsidated into the assembling capsid. Capsid proteins and the constituents may be combined simultaneously in vitro for the formation of packaged AAV capsids ready for transfer.

ENCAPSIDATED COMPONENTS

Molecules which may be packaged by the AAV capsids and subsequently transferred into cells include recombinant AAV genomes, which advantageously may then integrate into the target cell genome, and other heterologous DNA molecules. RNA, proteins and peptides, or small organic molecules, or combinations of the same, may also be encapsidated and transferred. Native molecular constituents are defined as those found in a wild-type AAV infection such as the AAV DNA genome, AAV RNA or AAV viral proteins. Heterologous molecules are defined as those that are not naturally found in an AAV infection; i.e., those not encoded by the AAV genome.

In a preferred embodiment of the present invention, the segment of DNA to be encapsidated may be linked to the AAV ITR sequences which contain the viral packaging signals and introduced into a host cell in which the AAV capsids are produced, and this segment may then be packaged into the AAV capsid. Such segments of DNA may encode genes or heterologous viral genomes. The inclusion of the packaging signal increases the efficiencies of encapsidation.

In an embodiment that allows for the integration of the packaged DNA into the host cell genome, the DNA may be linked to the AAV integration sequences (ITRS) that will target these sequences for integration into the host cell chromosome 19.

ASSOCIATION OF HETEROLOGOUS MOLECULES WITH AAV CAPSIDS

The invention is further directed to the association of therapeutically useful molecules with the outside of AAV capsids for efficient transfer of said molecules into host target cells. Such associated molecules may include DNA, RNA, proteins or peptides. In an embodiment of the invention the therapeutically useful molecules can be covalently linked to the capsid proteins. Alternatively, AAV capsid proteins may be genetically engineered to code for fusion capsid proteins to which associating molecules may bind.

RECOMBINANT AAV CAPSIDS AS EPITOPE CARRIERS

The invention is further directed to the production of AAV capsids by any of the above methods that are engineered to carry a heterologous epitope within any of the three capsid proteins, VP1, VP2or VP3. In this embodiment, DNA encoding a capsid protein is engineered by standard techniques in molecular biology, including but not limited to site-directed mutagenesis or polymerase chain reaction (PCR) mutagenic techniques, to incorporate a heterologous sequence that encodes an epitope from a clinically relevant antigen. This will result in the expression of a capsid fusion protein. The foreign is epitope preferably engineered into a region of the capsid protein that does not interfere with capsid formation.

Examples of antigens which may be the source of these epitopes include those from bacterial, viral or cellular origin. Antigens from bacteria include those from Salmonella, Staphylococcus, Streptococcus, cholera and mycobacterium (TB). Examples of antigens from viruses include the env protein of HIV, HA protein of influenza, hepatitis surface antigen, herpes glycoprotein, and the surface antigen of human papilloma virus. Examples of antigens from cellular sources include those identified as tumor-specific antigens in cancer, for example the carcinoembryonic (CEA) antigen found in colon cancer or the PSA antigen found in prostate cancer. Additionally, antigens corresponding to anti-immunoglobulin sequences that could be used to raise antibodies that would neutralize those in autoimmune disorders, including but not limited to multiple sclerosis, lupus erythematosus, diabetes, and scleroderma are within the scope of the invention.

USE OF AAV VEHICLES

The AAV capsid vehicles can be administered to a patient at therapeutically effective doses. A therapeutically effective dose refers to that amount of the compound sufficient to result in amelioration of symptoms of disease.

Toxicity and therapeutic efficacy of the AAV capsid vehicles can be determined by standard pharmaceutical procedures in cell cultures or experimental animals, e.g., for determining the $LDS_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Doses which exhibit large therapeutic indices are preferred. While doses that exhibit toxic side effects may be used, care should be taken to design a delivery system that targets such AAV capsid vehicles to the site of treatment in order to minimize damage to untreated cells and reduce side effects.

The data obtained from cell culture assays and animal studies can be used in formulating a range of dosage for use in humans. The dosage of such capsid vehicles lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection or a half-maximal inhibition) as determined in cell culture. Such information can be used to more accurately determine useful doses in humans. Levels in plasma may be measured, for example, by high performance liquid chromatography.

Pharmaceutical compositions comprising the AAV capsid vehicles, for use in accordance with the present invention, may be formulated in conventional manner using one or more physiologically acceptable carriers or excipients. For example, the AAV capsid vehicles may be suspended in a carrier such as PBS (phosphate buffered saline).

The AAV capsid vehicles and their physiologically acceptable salts and solvates may be formulated for administration by inhalation or insufflation (either through the mouth or the nose) or for oral, buccal, parenteral or rectal administration.

For administration by inhalation, the AAV capsid vehicles for use according to the present invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a therapeutic compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

The AAV capsids may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The AAV capsid vehicles may also be formulated in rectal compositions such as suppositories or retention enemas, e.g. containing conventional suppository bases such as cocoa butter or other glycerides.

In addition to the formulations described previously, the AAV capsid vehicles may also be formulated as a depot preparation. Such long acting formulations may be administered by implantation (for example, subcutaneously or intramuscularly) or by intramuscular injection. Thus, for example, the therapeutic compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example, comprise metal or plastic foil, such as a blister pack. The pack or dispenser device may be accompanied by instructions for administration.

EXAMPLE: PRODUCTION OF AAV CAPSIDS FROM RECOMBINANT ADENOVIRUS

Construction of DL324/CMV Cap

Figure 2:
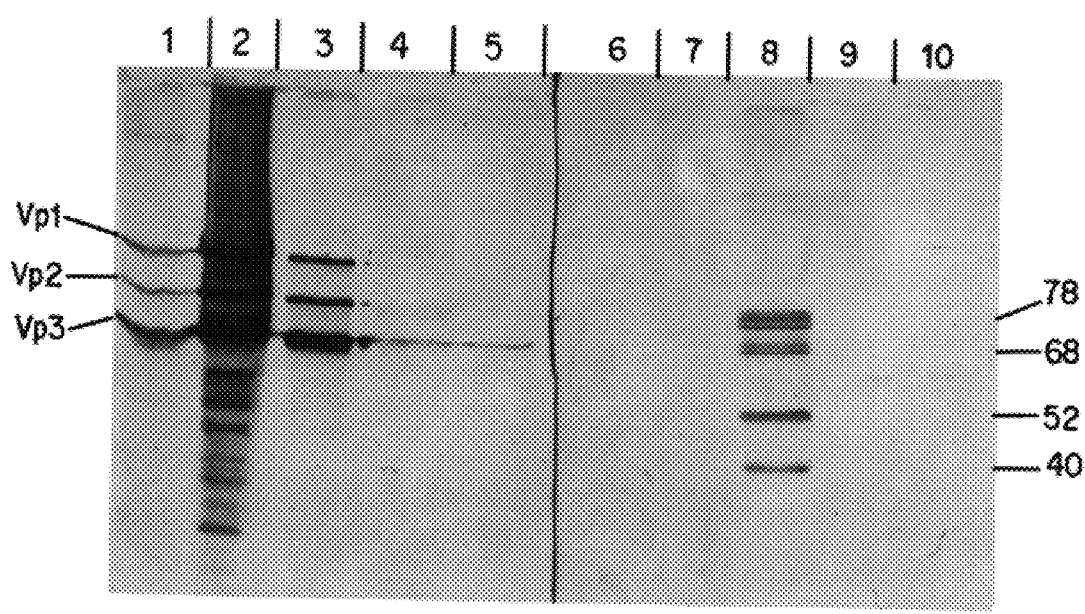
FIG. 2. Immunoblot of products of d1324/CMV/Cap expression in 293 cells. Lanes 1–5 were probed with anti-AAV2, lanes 6–10 were probed with anti-Rep. Lanes 1 and 6: pCAD/Cap; lanes 2 and 7: d1324/CMV/Cap; lanes 7 and 8: Ad+AAV2; lanes 4 and 9; Ad; lanes 5 and 10: Mock.

The AAV2 capsid coding region of psub201 (Samulski, R. J., et al., J. Virol. 61:3096–3101, 1987) was cloned into pCMV-Ad (Dolph, P. J., J.Virol. 62:2059–2066, 1988) to derive a plasmid (pCAD/Cap) in which the capsid genes were under the control of the CMV promoter. This plasmid was co-transfected with the linearized DNA fragment of adenovirus d1324 into 293 cells to create d1324/CMV/Cap, a recombinant denovirus containing the AAV2 capsid genes (FIG. 1). Plaques resulting from the infection of this virus into 293 cells were picked and screened for the expression of the AAV2 capsid proteins. One isolate (d1324/CMV/CapFF) was expanded into a viral stock for further analysis (FIG. 2). Correct splicing of the capsid messages occurred to give rise to the three capsid proteins (VP1, VP2, and VP3) in levels that mimicked those seen in a wild-type infection (5% VP1, 5% VP2, and 90% VP3).

GROWTH CHARACTERISTICS OF DL324/CMV/CAPFF

Figure 3:
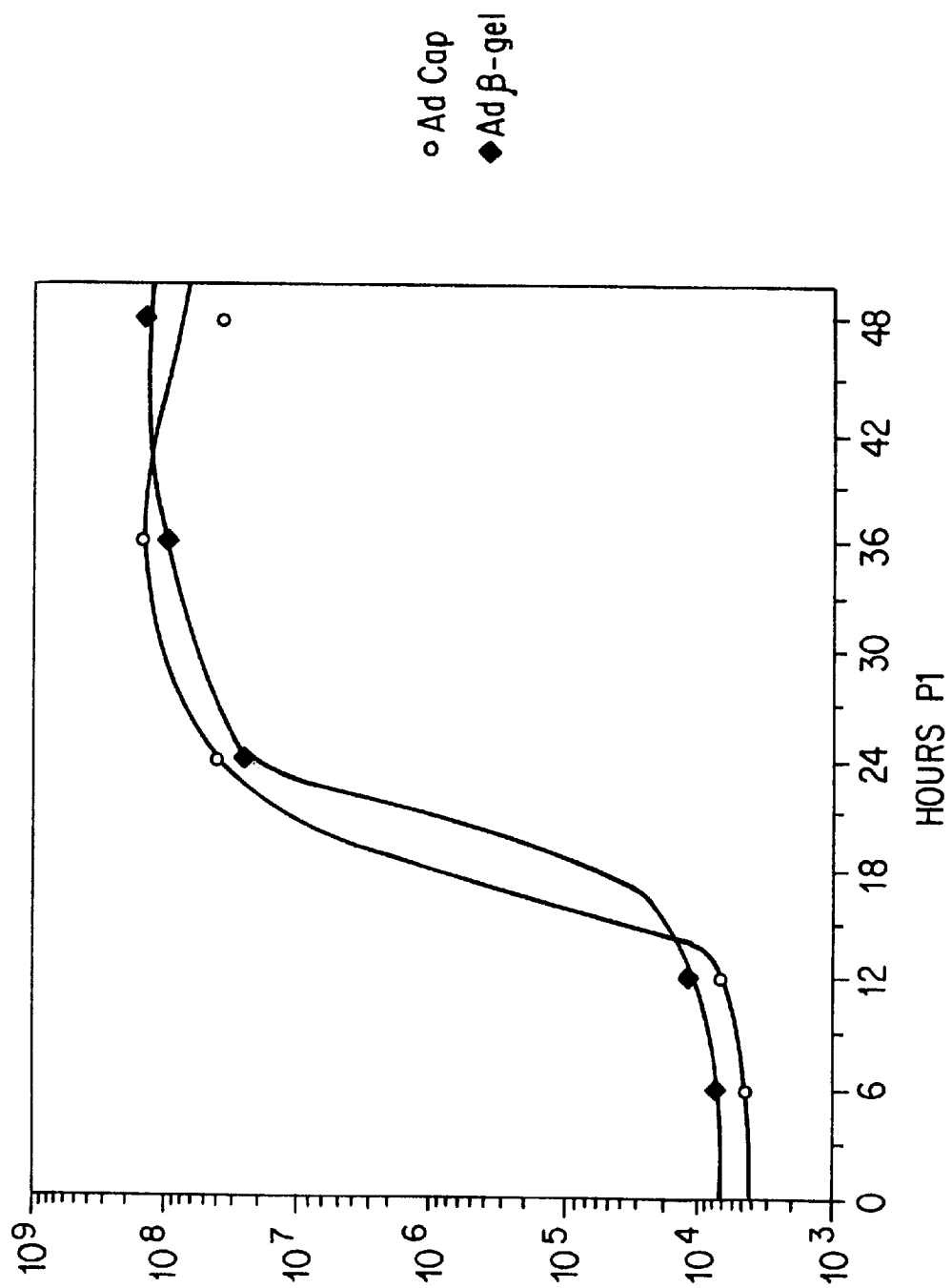
FIG. 3. Results of a one-step growth curve of d1324/CMV/Cap and Ad-βgal. At the times indicated on the X-axis, virus was collect from infected 293 cells and a plaque assay was performed to determine the titer (pfu/ml) shown on the Y-axis. This is the average result of two experiments.

The recombinant adenovirus was tested for its ability to exhibit wild-type growth in 293 cells. Cells were infected at an MOI of 200 particles per cell, sufficient to cause one-step growth. The control virus was recombinant adenovirus containing the B-gal gene, d1324-Bgal. Results over a 48-hr period demonstrated that the Ad-AAV recombinant virus had similar one-step growth characteristics to the control virus (FIG. 3).

TEMPORAL EXPRESSION OF THE CAPSID PROTEINS FROM ADIAAV VIRUS

Figure 4:
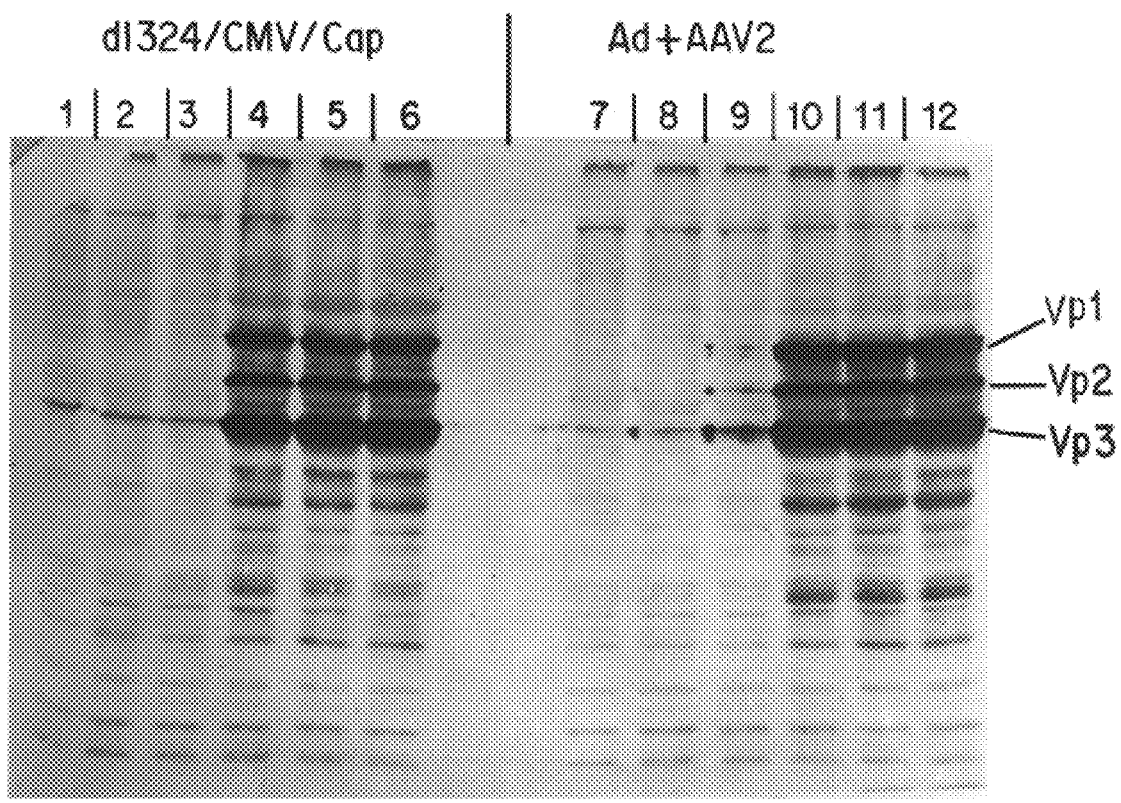
FIG. 4. d1324/CMV/Cap Capsid expression time course. 293 cells were infected with equal amounts of d1324/CMV/Cap and collected at various time points post infection. Capsid expression was detected by immunoblot. Lanes 1 and 7: Oh post infection; lanes 2 and 8: 6h post infection; lanes 3 and 9: 12h post infection; lanes 4 and 10: 24h post infection; lanes 6 and 11: 36h post infection; lanes 7 and 12: 48h post infection. The right-hand side of the blot shows the results from a parallel Ad+AAV2 infection.

To assess if the capsid proteins were expressed in a temporal manner similar to wild-type AAV, 293 cells were infected with the recombinant virus and samples were collected over a 48-hr course of infection. Immunoblotting demonstrated that the temporal expression of the AAV capsid proteins lagged only slightly behind that of wild-type AAV (FIG. 4).

mRNA PROCESSING IN AN AD/AAV INFECTION

Figure 5A:
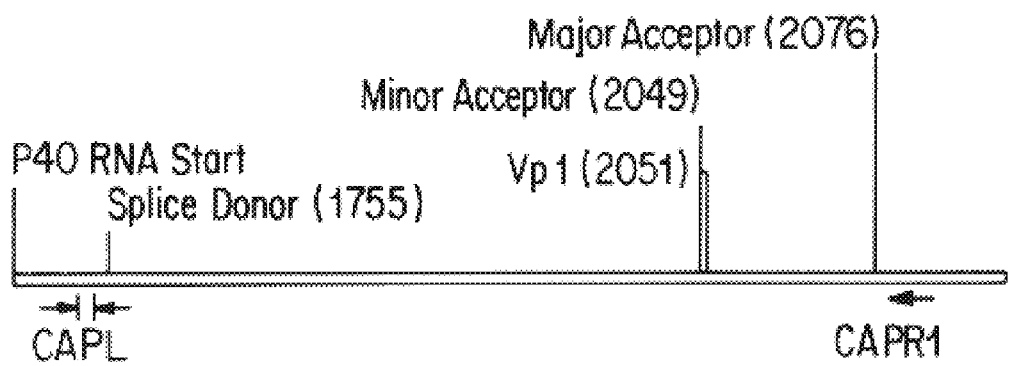
FIGS. 5A–5B. Splicing of AAV2 capsid messages expressed from d1324/CMV/Cap. mRNA from infected 293 cells was isolated and synthesized into cDNA. This cDNA was then amplified, in the presence of a-$^{32}$P-dCTP using the primers CAPL and CAPR1. The products were separated on 10% polyacrylamide gels and visualized by autoradiography. Lane 1: Ad+AAV2; lane 2: d1324/CMV/Cap.
Figure 5B:
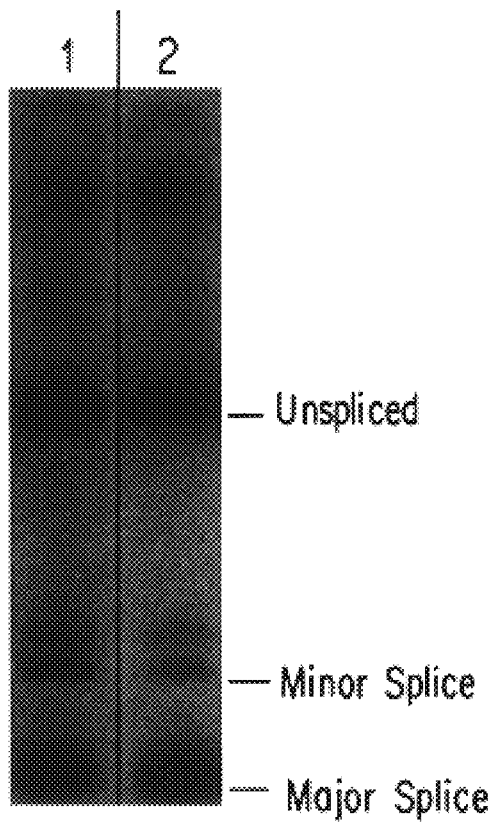

To determine if the capsid RNA was correctly spliced to yield the appropriate mRNAs corresponding to the three capsid proteins, RT-PCR performed on mRNAs isolated from infected 293 cells revealed the presence of the correctly spliced mRNAs, identical to those seen in a wild-type infection (FIG. 5).

SUBCELLULAR LOCALIZATION OF THE AAV CAPSID PROTEINS EXPRESSED FROM AD/AAV VIRUS

Figure 6A:
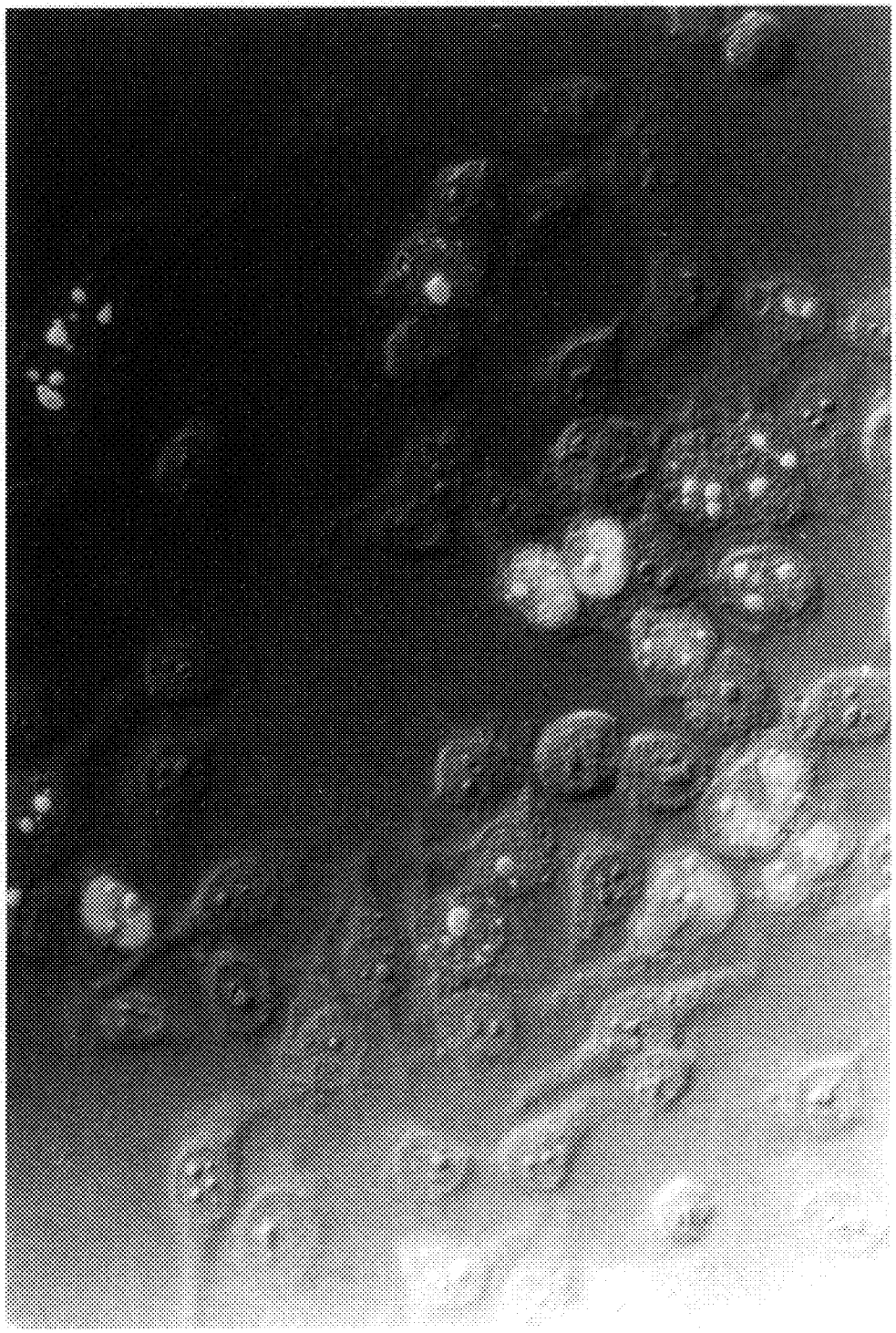
FIGS. 6A–6B. Immunofluorescence of AAV2 capsid and Rep proteins. HeLa cells infected with d1324/CMV/Cap in the absence (FIG. 6A) or presence (FIG. 6B) of Rep protein expression.
Figure 6B:
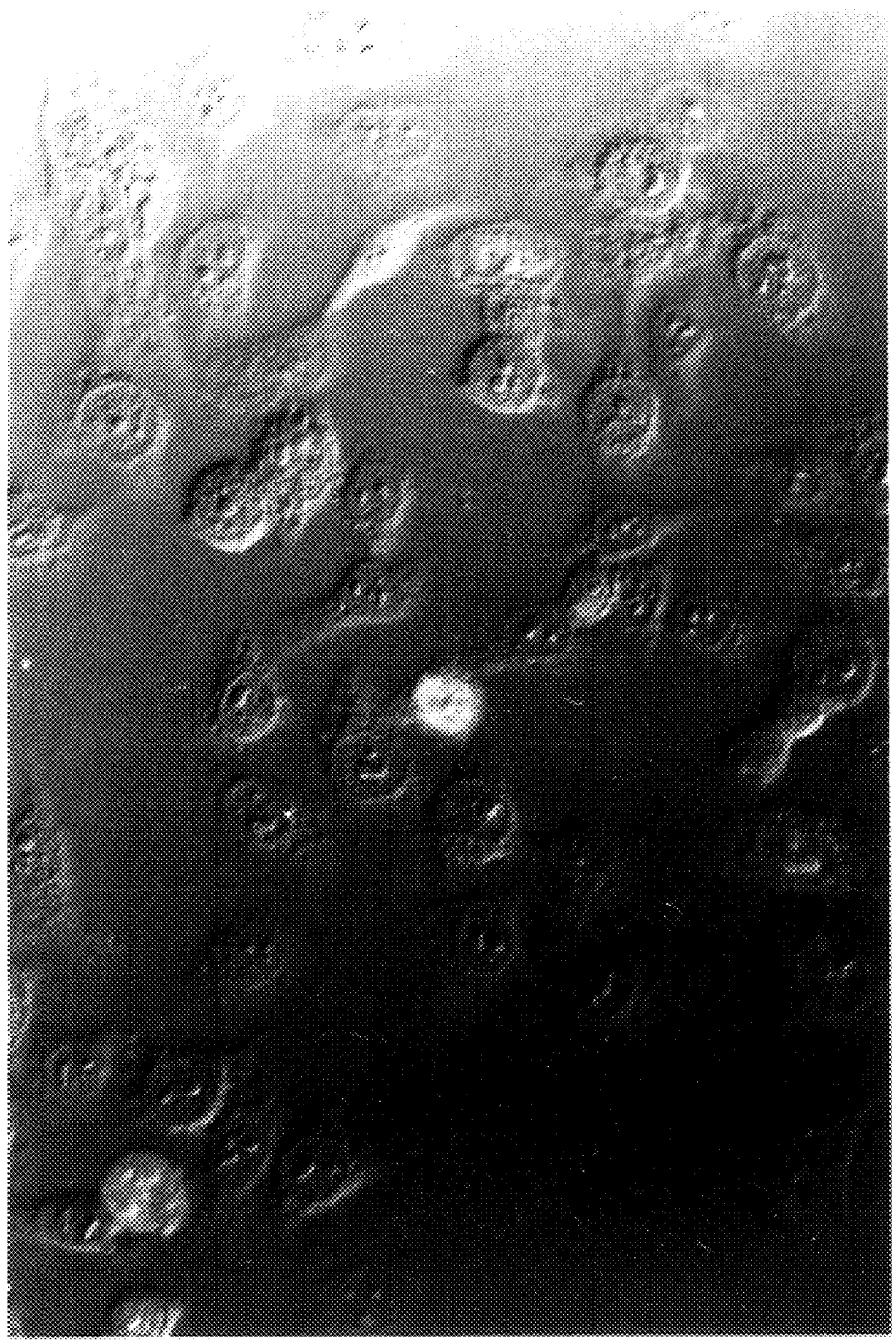

To determine if the capsid proteins expressed from the recombinant virus were correctly localized, immunofluorescence of HeLa cells infected with the virus was performed. Using an anti-AAV capsid antibody (Hoggan, R., et al., Proc. Natl. Acad. Sci. USA 55:1460–1474, 1966), distinct areas of staining concentration within the nucleus were seen, similar to that visualized in a wild-type AAV infection (FIGS. 6A and 6B).

FORMATION OF EMPTY VIRAL PARTICLES IN THE AD/AAV INFECTION

Figure 7:
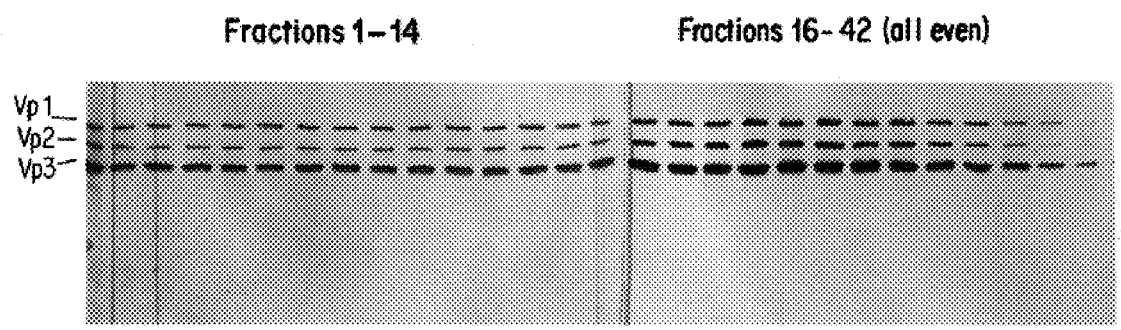
FIG. 7. Capsid immunoblot of CsCl density gradient fractions.

Viral lysates from 293 cells infected with d1324/CMV/Cap were banded by isopycnic centrifugation in a CsCl density gradient. Fractions from the gradient were immunoblotted with anti-AAV capsid antibody to localize the presence of the AAV capsid proteins (FIG. 7). Density measurements were calculated for the fractions (14–30) that exhibited the highest levels of AAV capsid proteins. The density of these fractions was 1.31 g/ml, which agrees with density measurements reported for empty viral particles (Myers, M. W. and Carter, B. J., Virology 102:71–82, 1980).

Figure 8:
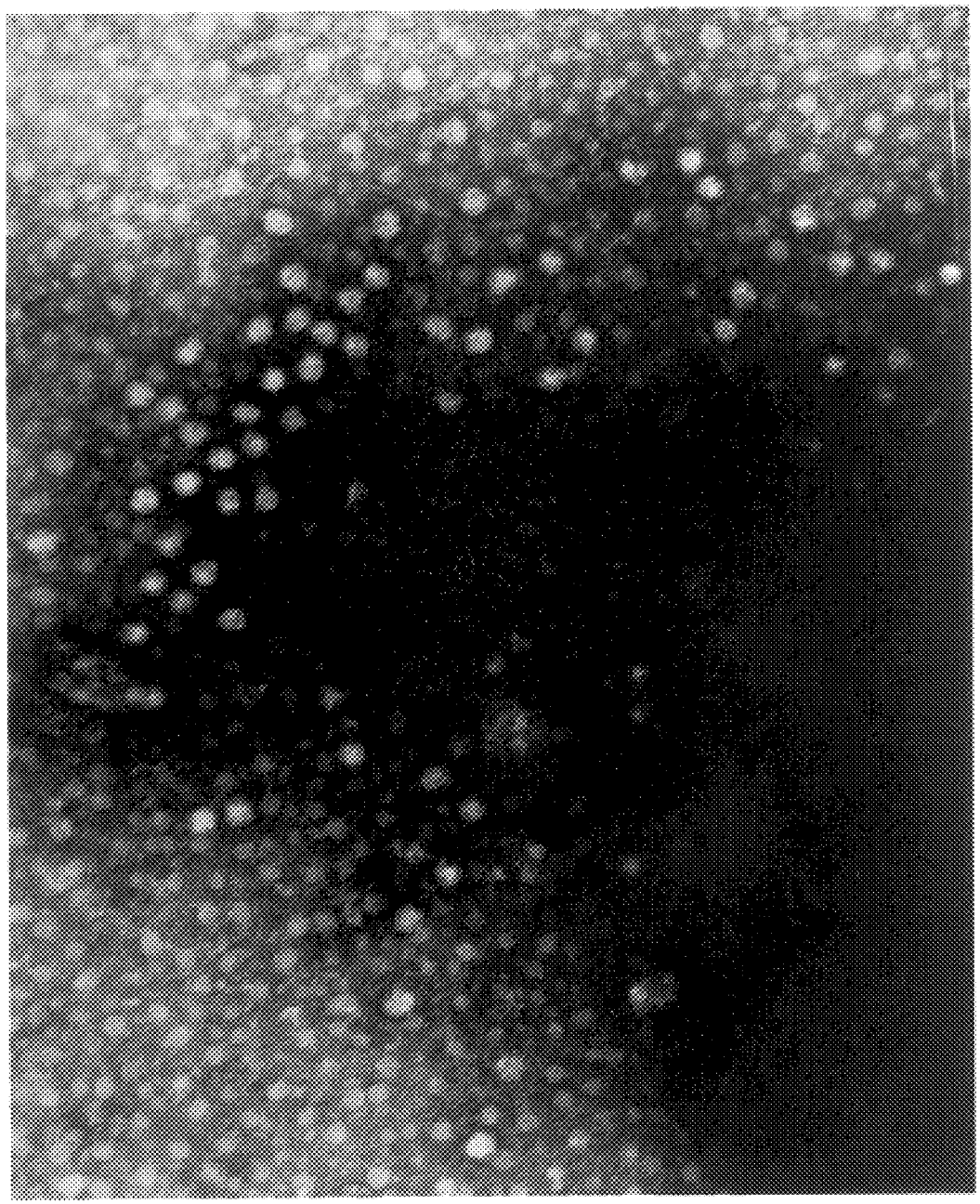
FIG. 8. Electron micrograph of empty capsids expressed from d1324/CMV/Cap. Mag. 250,000.

Further characterization by transmission electron microscopy demonstrated that the average diameter of these particles was 20 nm, typical for wild-type AAV2 particles (FIG. 8).

EXAMPLE: PACKAGING OF AAV VECTOR DNA MOLECULE USING ADENOVIRUS HYBRID CARRYING AAV CAPSID GENES

The following subsection below describes experiments demonstrating the in vivo encapsidation of AAV vector DNA into viral capsids in cells infected with the recombinant Ad/CMV/CAP virus.

MATERIALS AND METHODS

Plasmids and Virus

Plasmid pAB11 is the psub2ol plasmid, previously described in Samulski et al., 1987 J. Virol. 61:3096–3101, carrying an inserted lacZ reporter gene. Plasmid pAd/AAV codes for both the REP and CAP proteins (Samulski et al., 1989, J. Virol. 63:3822–3828). Plasmid pUHD RepA is a psub2ol derivative expressing only the AAV Rep proteins under the control of the tetracycline repressor promoter. The pUGD construct contains the AAV coding sequences for REP which includes AAV nucleotides 321–2234. The tetracycline repressor promoter inducer plasmid, pUHD 15–1 is described in Gossen and Buyard, 1992, Proc. Natl Acad. Sci. USA 89:5547–5551.

Transfection and Infection of Cells

Human 293 cells were transfected with 2 ug pAB11 and 12 μg pUHD 15–1. After 12 hours the monolayer cell culture was infected with Ad/CMV/CAP at 5 plaque forming units (PFU) per cell. 48 hours post-infection viral lysates were made. The control experiment consisted of transfection of 293 cells with 2 μg pAB11, 12 μG pAd/AAV followed by infection with 5 pfu per cell wild type adenovirus (WT300).

200λ of the above lysates were used to infect a new monolayer of 293 cells. 24 hours post-infection the cells were stained for beta galactosidase activity. In addition, as an additional control, wild type Adenovirus was mixed with the pAB11 plasmid DNA.

RESULTS

Figure 9A:
FIGS. 9A–9B. 293 cells were transfected/infected (FIG. 9A, panel 1 and FIG. 9B, panel 1) with 10 ug/per 10 cm dish, pAB11 plasmid DNA and 5 pfu wild type adenovirus. 293 cells were infected with 200 ul viral lysate from ad/CMV/CAP complementation system (panel 2 of FIGS. 9A and 9B) or from pAd/AAV helper system (panel 3 of FIGS. 9A and 9B). LacZ histochemical analysis of infected cells were assayed at 24 hours (EMBO 5:3133, 1986). Photographs were taken at a magnification of 10× for panel 1A or 20x for the remainder of the panels. Each panel represents an individual field from an infected dish of cells.
Figure 9B:

After staining the infected cells for beta galactosidase activity, positive staining was observed with viral lysates utilizing the Ad/CMV/CAP helper virus as a source of AAV capsid protein and with the pAd/AAV helper plasmid which express both rep and cap genes (panel 2 of FIGS. 9A–9B). There was no detection of beta galactosidase activity in any cells infected with wild type Adenovirus and pAB11.

These results indicate that AAV lacZ DNA may be rescued from the plasmid, replicated and packaged into AAV particles using either the traditional packaging system or the Ad/CMV/CAP virus stock. These results clearly demonstrate the potential for generating infectious AAV particles using the adenovirus hybrid virus as a source for producing AAV capsid proteins.

The present invention is not to be limited in scope by the specific embodiments described which are intended as single illustrations of individual aspects of the invention, and functionally equivalent methods and components are within the scope of the invention. Indeed, various modifications of the invention, in addition to those shown and descried herein will become apparent to those skilled in the art from the foregoing descriptions and accompanying drawings. Such modifications are intended to fall within the scope of the appended claims.

What is claimed is:

1. A method for transferring a molecule into a cell, comprising contacting the cell with an adeno-associated virus capsid vehicle in which a heterologous RNA molecule is covalently linked, bound to, or encapsidated, with adeno-associated virus capsid proteins.

2. A method for transferring a molecule into a cell, comprising contacting the cell with an adeno-associated virus capsid vehicle in which a heterologous protein is covalently linked, bound to, or encapsidated, with adeno-associated virus capsid proteins.

3. A method for transferring a molecule into a cell, comprising contacting the cell with an adeno-associated virus capsid vehicle in which a heterologous peptide is covalently linked, bound to, or encapsidated, with adeno-associated virus capsid proteins.

* * * * *